United States Patent [19]

Archer

[11] 4,327,224

[45] Apr. 27, 1982

[54] α-[(ALKYLAMINO)ALKYL]-4-HYDROXY-3-(ALKYLTHIO)BENZENEMETHANOLS, DERIVATIVES THEREOF AND INTERMEDIATES THEREFOR

[75] Inventor: Sydney Archer, Bethlehem, N.Y.

[73] Assignee: Sterling Drug Inc., New York, N.Y.

[21] Appl. No.: 700,036

[22] Filed: Jun. 25, 1976

[51] Int. Cl.³ .............................................. C07C 69/14
[52] U.S. Cl. .............................. 560/142; 260/343.7; 260/501.12; 260/501.17; 260/501.19; 424/254; 424/262; 424/263; 424/280; 424/308; 424/311; 424/316; 424/330; 544/299; 560/109; 564/285; 564/344; 564/363; 564/364
[58] Field of Search .................. 260/479 R, 477, 570.6

[56] References Cited

U.S. PATENT DOCUMENTS

| | | | |
|---|---|---|---|
| 3,917,704 | 11/1975 | Kaiser | 260/570.6 |
| 3,954,871 | 5/1976 | Buu-Hor et al. | 260/570.6 |
| 3,976,694 | 8/1976 | Kaiser | 260/570.6 |

OTHER PUBLICATIONS

Kaiser et al., J. Med. Chem., 1975, vol. 18, No. 7, p. 674.

*Primary Examiner*—Robert V. Hines
*Attorney, Agent, or Firm*—Paul E. Dupont; B. Woodrow Wyatt

[57] ABSTRACT

Alpha-[(lower alkylamino)alkyl]-4-hydroxy-3-(alkylthio, akylsulfinyl or alkylsulfonyl)benzenemethanols which have β-adrenergic blocking activity and which are therefore useful in controlling tachycardia are prepared by reduction of the corresponding (lower alkylamino)alkyl 4-hydroxy-3-(akylthio, akylsulfinyl or alkylsulfonyl)phenyl ketones.

14 Claims, No Drawings

α-[(ALKYLAMINO)ALKYL]-4-HYDROXY-3-(AL-KYLTHIO)BENZENEMETHANOLS, DERIVATIVES THEREOF AND INTERMEDIATES THEREFOR

BACKGROUND OF THE INVENTION

1. Field of the Invention

The present invention relates to compositions of matter classified in the art of chemistry as α-[(lower alkylamino)alkyl]-4-hydroxy-3-(alkylthio, alkylsulfinyl or alkylsulfonyl)benzenemethanols, to processes and intermediates for the preparation thereof, and to a method of using the same for controlling tachycardia in mammals.

2. Prior Art

Continental Pharma British Specification No. 1,321,701, published June 27, 1973, discloses a group of compounds embraced by the generic formula:

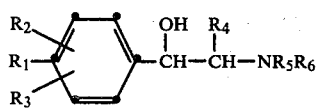

wherein, inter alia:
R$_1$ is RS, RSO or RSO$_2$ (R=H, or C$_1$–C$_{10}$ alkyl);
R$_2$ and R$_3$ are hydrogen, C$_1$–C$_4$ alkoxy or C$_1$–C$_4$ alkylthio;
R$_4$ is hydrogen or C$_1$–C$_4$ alkyl; and
R$_5$ and R$_6$ are independently hydrogen or C$_1$–C$_{16}$ alkyl.

The compounds are stated to exhibit β-adrenergic blocking, peripheral vasodilator, anti-arrhythmic and hypotensive activities.

Kaiser and Ross U.S. Pat. No. 3,917,704 issued Nov. 4, 1975, discloses a group of α-aminoalkyl-4-hydroxy-3-alkylsulfonylmethylbenzyl alcohols having the formula:

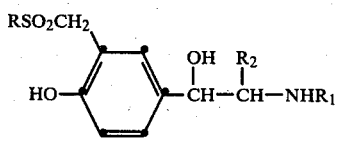

wherein, inter alia:
R represents lower alkyl of from 1 to 5 carbon atoms, straight or branched chain;
R$_1$ represents a branched chain lower alkyl group of from 3 to 5 carbon atoms; and
R$_2$ represents hydrogen, methyl or ethyl.

The compounds are stated to have utility as β-adrenergic stimulants with relatively greater activity on respiratory smooth muscle than on cardiac muscle.

Kaiser, et al., J. Med. Chem. 18, 674–683 (1975) report essentially the work described in above-identified Kaiser and Ross U.S. Pat. No. 3,917,704 and in addition disclose the compound having the formula:

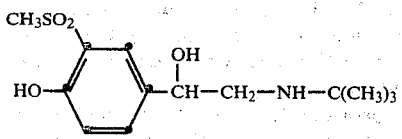

which is stated to be weakly active as a β-adrenergic agonist and which exhibits β-adrenergic antagonistic activity. The work described in the Kaiser publication was reported orally Apr. 10, 1975 at the 169th national meeting of the American Chemical Society. An abstract of the oral presentation appeared at Abstracts of Papers, ACS Meeting 169: Medi 54 (April, 1975).

Lutz et al., J. Med. Chem. 15, 795–802 (1972), disclose the attempted preparation of 4-hydroxy-3-mercaptophenylethanolamine, i.e.:

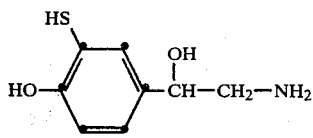

The compound however was neither isolated as a single entity nor characterized.

Pratesi, et al., British Specification 1,154,193 published June 4, 1969 discloses as a β-adrenergic agent α-[(isopropylamino)methyl]-3-(methylthio)benzenemethanol, i.e.:

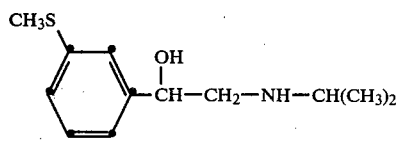

SUMMARY OF THE INVENTION

The present invention provides novel, therapeutically useful compounds which have β-adrenergic blocking activity and which are therefore indicated for use in controlling tachycardia which is either drug-induced or the result of a physiological condition.

In a composition of matter aspect the invention relates to certain α-[(lower alkylamino)alkyl]-4-YO-3-(lower alkylthio, lower alkylsulfinyl or lower alkylsulfonyl)benzenemethanols which have useful β-adrenergic blocking activity.

In another composition of matter aspect the present invention provides (lower alkylamino)alkyl 4YO-3-(lower alkylthio, lower alkylsulfinyl or lower alkylsulfonyl)phenyl ketones which are useful as intermediates in the preparation of the corresponding benzenemethanols.

In one of its process aspects this invention relates to a process for preparing α-[(lower alkylamino)alkyl]-4-YO-3-(lower alkylthio, lower alkylsulfinyl or lower alkyl-sulfonyl)benzenemethanols which comprises reducing certain (lower alkylamino)alkyl 4-YO-3-(lower alkylthio, lower alkyl-sulfinyl or lower alkylsulfonyl)-phenyl ketones.

In another process aspect the present invention provides a process for preparing (lower alkylamino) alkyl 4-YO-3-(lower alkylthio, lower alkylsulfinyl or lower alkylsulfonyl)phenyl ketones which comprises reacting certain haloalkyl 4-YO-3-(lower alkylthio, lower alkylsulfinyl or lower alkylsulfonyl)phenyl ketones with certain lower alkylamines.

In yet another process aspect this invention relates to a process for preparing certain α-[(lower alkylamino)alkyl]-4-YO-3-(lower alkylsulfinyl)benzenemethanols which comprises oxidizing the corresponding α-[(lower alkylamino)alkyl]-4-YO-3-(lower alkylthio)benzenemethanols.

In a method aspect the present invention provides a method of controlling tachycardia in mammals which comprises administering to said mammals a therapeutically effective amount of an α-[(lower alkylamino)alkyl]-4-YO-3-(lower alkylthio, lower alkylsulfinyl or lower alkylsulfonyl)benzenemethanol of the invention.

DETAILED DESCRIPTION INCLUSIVE OF THE PREFERRED EMBODIMENTS

More specifically the invention sought to be patented resides, in a composition of matter aspect, in α-[(lower alkylamino)alkyl]-4-YP-3-(lower alkylthio, lower alkylsulfinyl or lower alkylsulfonyl)benzenemethanols which have useful β-adrenergic blocking activity having Formula I hereinbelow:

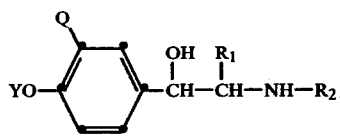

wherein:
$R_1$ is hydrogen, methyl or ethyl;
$R_2$ is lower alkyl;
Q is lower alkylthio, lower alkylsulfinyl or lower alkylsulfonyl;
Y is hydrogen, lower alkanoyl, benzoyl or benzoyl substituted with from 1 to 2 methyl groups; and acid-addition salts thereof.

In a further composition of matter aspect the invention sought to be patented resides in (lower alkylamino)-alkyl 4-YO-3-(lower alkylthio, lower alkylsulfinyl or lower alkylsulfonyl)phenyl ketones having Formula II hereinbelow:

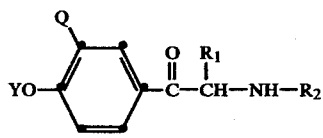

wherein $R_1$, $R_2$, Q and Y have the above-given meanings; and acid-addition salts thereof. These compounds are useful as intermediates in the preparation of the corresponding benzenemethanols of Formula I hereinabove.

The invention sought to be patented resides, in a process aspect, in the process for producing the benzene-methanols of Formula I hereinabove which comprises reducing the (lower alkylamino)alkyl phenyl ketones having Formula II hereinabove.

In another process aspect the invention sought to be patented resides in the process for producing the (lower alkylamino)alkyl phenyl ketones of Formula II hereinabove which comprises reacting a haloketone having Formula III hereinbelow:

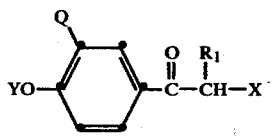

wherein $R_1$, Q and Y have the previously given meanings and X is chloro or bromo with a lower alkylamine having the formula $R_213\ NH_2$ wherein $R_2$ has the previously given meaning.

In a further process aspect the invention sought to be patented resides in the process for producing the 3-(lower alkylsulfinyl)benzenemethanols of Formula I hereinabove, wherein $R_1$, $R_2$ and Y have the above-given meanings and Q is lower alkylsulfinyl which comprises oxidizing the 3-(lower alkylthio)benzenemethanols of Formula I wherein $R_1$, $R_2$ and Y have the above-given meanings and Q is lower alkylthio.

In a method aspect the invention sought to be patented resides in the method of controlling tachycardia in mammals which comprises administering to said mammals a therapeutically effective amount of a benzenemethanol of Formula I hereinabove.

In the terms lower alkyl, lower alkylthio, lower alkylsulfinyl and lower alkylsulfonyl "lower" denotes an alkyl moiety having from 1 to 4 carbon atoms which can be arranged as straight or branched chains. There are included methyl, ethyl, n-propyl, isopropyl, n-butyl, sec-butyl, and the like, methyl and ethyl being preferred.

By "lower alkanoyl" is meant straight or branched-chain alkanoyl radicals containing from 1 to 6 carbon atoms as illustrated by formyl, acetyl, propionyl, butyryl, isobutyryl, pivalyl, caproyl and the like.

It will be appreciated that Y in Formulas I and II can represent acyl residues other than the above without departing from the spirit of the present invention since it is well known that such esters undergo hydrolytic cleavage under physiological conditions to produce in situ the parent phenols which, of course, have the previously indicated biological activity.

In accordance with one of the process aspects of this invention, the benzenemethanols represented by Formula I hereinabove are obtained by reducing the (lower alkylamino)-alkyl phenyl ketones of Formula II with an appropriate reducing agent in a suitable solvent as for example sodium borohydride or lithium borohydride in water or a lower alkanol; lithium aluminum hydride in ether, tetrahydrofuran or dioxane; diborane in tetrahydrofuran or diglyme; aluminum isopropoxide in 2-propanol; or by hydrogenation in the presence of a noble metal catalyst such as palladium or platinum.

When the (lower alkylamino)alkyl phenyl ketone contains a carboxylic ester group (Formula II wherein Y is lower alkanoyl or benzoyl), and it is desired to retain the ester group in the reduction product (Formula I wherein Y is lower alkanoyl or benzoyl), the use of reducing means resulting in reduction of carboxylic ester groups should of course be avoided. Accordingly in such instances reduction is preferably effected with an alkali metal borohydride or by catalytic hydrogenation which reducing means result in selective reduction of the ketone function. When the ultimately desired product is the free phenol (Formula I wherein Y is hydrogen) the above reduction reaction can be followed by hydrolysis of the ester group, or alternatively, the esterified (lower alkylamino)alkyl phenyl ketone (Formula II wherein Y is lower alkanoyl or benzoyl) can be reduced with a reagent capable of reducing both ketone and carboxylic ester functions e.g. lithium aluminum hydride.

The borohydride reduction method is conveniently carried out by treating the (lower alkylamino)alkyl phenyl ketone with sodium borohydride in methanol at about −10° C. to 65° C. for approximately 15 minutes to 2.5 hours or until reduction is substantially complete as indicated by thin layer chromatography. If the starting material contains an ester group (Formula II wherein Y is lower alkanoyl or benzoyl) and it is desired to retain the latter in the final product, the reaction mixture is quenched with acid and the esterified benzenemethanol (Formula I wherein Y is lower alkanoyl or benzoyl) is isolated in conventional fashion. If on the other hand the free phenol (Formula I wherein Y is hydrogen) is desired the reaction mixture is treated with an equivalent of sodium or potassium hydroxide in water and stirred at about 20° C. to ;b 65° C. for approximately 30 minutes to 15 hours. The resulting phenol is isolated in a conventional manner.

The catalytic hydrogenation process is conveniently carried out in a suitable solvent, for example N,N-dimethylformamide, at 20° C.–50° C. under a hydrogen pressure of from 20–50 p.s.i. in the presence of a noble metal catalyst such as palladium. The hydrogenation is continued until the theoretical amount of hydrogen is absorbed. After removal of the catalyst, the reduction product is isolated in conventional fashion.

Although the 3-(lower alkylsulfinyl)benzenemethanols (Formula I wherein Q is lower alkylsulfinyl) can be obtained by reducing the corresponding ketones (Formula II wherein Q is lower alkylsulfinyl) according to the foregoing procedures, it is ordinarily preferred to prepare the sulfinyl compounds by oxidizing the corresponding sulfides (Formula I wherein Q is lower alkylthio).

Thus in accordance with another process aspect of the invention the 3-(lower alkylsulfinyl)benzenemethanols represented by Formula I hereinabove wherein Q is lower alkylsulfinyl are obtained by oxidizing the corresponding 3-(lower alkylthio)benzenemethanols (Formula I wherein Q is lower alkylthio) with an appropriate oxidizing agent such as a peracid, hydrogen peroxide or sodium metaperiodate.

The oxidation is preferably carried out by treating the 3-(lower alkylthio)benzenemethanol with commercial 50% peracetic acid in methanol at about −10° C. to 10° C. for approximately 15 minutes to 1.5 hours or until oxidation is substantially complete as indicated by thin layer chromatography.

Alternatively, oxidation is effected with 30% hydrogen peroxide in methanol at about 20° C. to 65° C. for from 24 to 72 hours or until oxidation is substantially complete as indicated by thin layer chromatography. The oxidation product is isolated according to conventional methods.

The (lower alkylamino)alkyl phenyl ketones of Formula II hereinabove are obtained in accordance with this invention by reacting a haloketone of Formula III with an excess of a lower alkylamine in a suitable solvent such as acetonitrile, dimethylsulfoxide, or N,N-dimethylformamide at about −65° C. to 25° C. for from 1 to 4 hours or until the reaction is substantially complete as indicated by thin layer chromatography.

In those instances wherein Y in Formula III is lower alkanoyl or benzoyl, reaction with a lower alkylamine may result in partial cleavage of the ester function. When desired the partially deacylated product can be re-esterified according to known procedures for example with an acyl halide in the presence of a strong acid such as trifluoroacetic acid.

Although the 3-(lower alkylsulfinyl)phenyl ketones (Formula II wherein Q is lower alkylsulfinyl) can be obtained by reacting a haloketone of Formula III wherein Q is lower alkylsulfinyl with an appropriate lower alkylamine it is generally preferred to prepare the 3-(lower alkylsulfinyl)phenyl ketones of Formula II by oxidation of the corresponding sulfides (Formulas II, Q is lower alkylthio) as described hereinabove for the preparation of the 3-(lower alkylsulfinyl)benzenemethanols (Formula I wherein Q is lower alkylsulfinyl.

The haloketones of Formula III are obtained by halogenating with chlorine or bromine the appropriate phenyl ketone having the Formula IV hereinbelow:

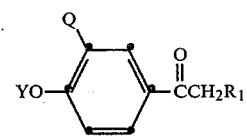

wherein $R_1$ and Q have the previously given meanings and Y is methyl, lower alkanoyl, benzoyl or benzoyl substituted by from 1 to 2 methyl groups. The reaction is conveniently carried out by treating the ketone of Formula IV in an inert solvent such as chloroform with bromine at approximately 25° C. optionally in the presence of an inorganic base e.g. calcium carbonate. The reaction generally has an induction period and in certain instances it may be advantageous to initiate the reaction by exposing the mixture to ultraviolet radiation until bromination has commenced as evidenced by decolorization and concomitant evolution of hydrogen bromide. If desired the Y substituent of the resulting haloketone can be removed according to well known procedures, for example by ester hydrolysis when Y is lower alkanoyl or benzoyl and by O-demethylation with a Lewis acid such as aluminum chloride, hydrogen bromide or boron tribromide when Y is methyl.

The phenyl ketones of Formula IV hereinabove can be obtained by a variety of procedures which are generally known in the art. Thus for example the 3-(lower alkylthio)phenyl ketones of Formula IV wherein Q is lower alkylthio and Y is lower alkanoyl or benzoyl are obtained by alkylation of the parent 3-mercapto-4-hydroxyphenyl ketones (Formula IV wherein Q is mercapto and Y is hydrogen) with an appropriate lower alkyl halide in a suitable solvent such as a lower alkanone in the presence of an acid acceptor e.g. an alkali metal carbonate, followed by esterification of the resulting 3-(lower alkylthio)-4-hydroxyphenyl ketone (Formula IV wherein Q is lower alkylthio and Y is hydrogen) with an appropriate acylating agent such as a lower alkanoyl or benzoyl halide or anhydride in an inert solvent such as methylene chloride, chloroform, benzene or toluene in the presence of an acid acceptor such as triethylamine or pyridine. The 3-mercapto-4-hydroxyphenyl ketones are in turn obtained by chlorosulfonation of the generally known 4-hydroxyphenyl ketones of Formula IV wherein Q and Y are hydrogen with excess chlorosulfonic acid at about 0° C. to 25° C. preferably in the absence of a solvent followed by reduction of the resulting 3-chlorosulfonyl-4-hydroxyphenyl ketones with a suitable reducing agent such as stannous chloride and hydrochloric acid, or zinc and sulfuric acid.

Alternatively the 3-(lower alkylthio)phenyl ketones of Formula IV wherein Q is lower alkylthio and Y is lower alkanoyl can be obtained by acylating the generally known o-(lower alkylthio)phenols with an appropriate acyl halide (i.e. R₁CH₂COX; X is chloro or bromo) under Friedel-Crafts conditions followed by esterification of the resulting 3-(lower alkylthio)-4-hydroxyphenyl ketones as described above.

It will be appreciated that although the 3-(lower alkylsulfinyl)phenyl ketones of Formula IV can be obtained by oxidizing the corresponding sulfides (Formula IV wherein Q is lower alkylthio) it is generally preferred to employ the latter as a starting material and to carry out any desired oxidation of sulfide to sulfoxide at a later stage in the synthesis as previously described.

The 3-(lower alkylsulfonyl)phenyl ketones of Formula IV wherein Q is lower alkylsulfonyl and Y is methyl are obtained by oxidizing the 3-(lower alkylsulfonyl)anisoles of Formula V hereinbelow:

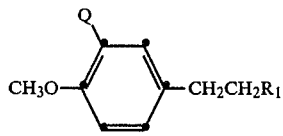

wherein R₁ has the previously given meaning and Q is lower alkylsulfonyl with an appropriate oxidizing reagent such as ammonium persulfate in the presence of silver nitrate in aqueous medium in the approximate temperature range 20° C. to 70° C. for about 2 to 3 hours. In turn the 3-(lower alkylsulfonyl)anisoles are obtained by sulfonating the generally known anisoles of Formula V wherein Q is hydrogen with an appropriate lower alkylsulfonic anhydride in an inert solvent e.g. sym-tetrachloroethane at about 130° C. to 180° C.

Due to the presence of the basic amino grouping, the free base forms of the final products represented by Formula I and also of the intermediates represented by Formula II react with organic and inorganic acids to form acid-addition salts. The compounds of the invention are useful both in the free base form and in the form of acid-addition salts, and both forms are within the purview of the invention. The acid-addition salts are simply a more convenient form for use, and in practice, use of the salt form inherently amounts to use of the base form.

The acid-addition salts are prepared from any organic or inorganic acid. They are obtained in conventional fashion, for instance either by direct mixing of the base with the acid, or, when this is not appropriate, by dissolving either or both the base and the acid separately in water or an organic solvent and mixing the two solutions, or by dissolving both the base and the acid together in a solvent. The resulting acid-addition salt is isolated by filtration, it is insoluble in the reaction medium, or by evaporation of the reaction medium to leave the acid-addition salt as a residue. The acid moieties or anions in these salt forms are in themselves neither novel nor critical and therefore can be any acid anion or acid-like substance capable of salt formation with the base.

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, dibenzoyltartaric acid, oxalic acid, pyromucic acid, citric acid, lactic acid, mandelic acid, glycolic acid, gluconic acid, saccharic acid, ascorbic acid, penicillin, benzoic acid, phthalic acid, salicyclic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacetic acid, barbituric acid, cyclohexylsulfamic acid, isethionic acid, methanesulfonic acid, benzenesulfonic acid, p-toluenesulfonic acid, 1,4-naphthalenedisulfonic acid, butylarsonic acid, methanephosphonic acid, acidic resins, hydrofluoric acid, hydrochloric acid, hydrobromic acid, hydriodic acid, perchloric acid, nitric acid, sulfuric acid, sulfamic acid, glutaric acid, phosphoric acid, arsenic acid, and the like.

All the acid-addition salts are useful as sources of the free base form, by reaction with an inorganic base. It will thus be appreciated that if one or more of the characteristics such as solubility, crystallinity molecular weight, physical appearance, toxicity, or the like of a given base or acid-addition salt thereof render that form unsuitable for the purpose at hand it can be readily converted, in accordance with procedures well known in the art, to another more suitable form.

When the compounds of the invention are to be utilized for pharmaceutical purposes, the acids used to prepare the acid-solution salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anions. Appropriate medicinally acceptable salts within the scope of the invention are those derived from acids such as hydrochloric acid, acetic acid, lactic acid, tartaric acid, cyclohexylsulfamic acid, methanesulfonic acid, phosphoric acid and the like.

The compounds of the invention represented by Formula I and Formula II wherein Y is hydrogen are of course amphoteric, having both acidic phenol and basic amino groups, and thus form salts with both acids and bases.

Due to the presence of at least one and as many as three asymmetric centers in the compounds of the invention represented by Formula I (i.e. the carbinol carbon atom, the carbon atom to which R₁, when methyl or ethyl, is attached, and the sulfur atom when Q is lower alkylsulfinyl), said compounds can exist in as many as eight stereochemically isomeric forms, all of which either individually or as mixtures of any two or more are considered within the purview of this invention. If desired, the isolation or the production of a particular stereochemical form or of a mixture of two or more stereochemical forms can be accomplished by application of general principles known in the art.

In carrying out the method aspect of this invention, i.e. the method of controlling tachycardia in mammals which comprises administering to said mammals a therapeutically effective amount of a compound having Formula I, said compounds can be administered orally in the form of pills, tablets, capsules, e.g. in admixture with talc, starch, milk sugar or other inert, i.e., non-toxic or pharmacologically acceptable pharmaceutical carrier, or in the form of aqueous solutions, suspensions, encapsulated suspensions, gels, elixirs, aqueous alcoholic solutions, e.g. in admixture with sugar or other sweetening agents, flavorings, colorants, thickeners and other conventional pharmaceutical excipients. When injected subcutaneously, intramuscularly, or intravenously, they can be administered, e.g., as an aqueous or peanut oil solution or suspension using excipients and carriers conventional for this mode of administration.

The best route of administration and the best dosage will be apparent from the laboratory tests for activity and toxicity of the selected compound conventionally undertaken as part of the development phase of a pharmaceutical.

The molecular structures of the compounds of the invention were assigned on the basis of the method of their preparation and study of their IR and NMR spectra, and confirmed by the correspondence between calculated and found values for the elemental analyses of representative examples.

The invention is further illustrated by the following examples without, however, being limited thereto.

EXAMPLE 1

A. To a stirred solution containing 61.4 g. (0.435 mole) of o-(methylthio)phenol and 35 g. (0.45 mole) of acetyl chloride in 170 ml. of nitrobenzene was added portionwise over a period of 20 minutes 80 g. (0.60 mole) of aluminum chloride. The reaction mixture was stirred overnight at room temperature and then one hr. at 65° C. The reaction mixture was cooled, diluted with ice and water and extracted with methylene chloride. The organic extracts were evaporated in vacuo, the residue diluted with ether and allowed to stand two days in the refrigerator. The precipitated product was collected and dried to give 27 g. of 4'-hydroxy-3'-(methylthio)acetophenone.

B. To a cooled, stirred solution containing 24.5 g. (0.134 mole) of 4'-hydroxy-3'-(methylthio)acetophenone and 21 g. (0.21 mole) of triethylamine in 400 ml. of methylene chloride was added dropwise over a period of 30 minutes 16.4 g. (0.21 mole) of acetyl chloride. After stirring overnight at room temperature the reaction mixture was washed with water, dried over anhydrous sodium sulfate, and concentrated to a small volume. The concentrate was diluted with ether and cooled in an ice bath. The resulting precipitate was collected to give 23.5 g. of 4'-hydroxy-3'-(methylthio)acetophenone 4'-acetate.

C. To a stirred mixture containing 23.2 g. (0.108 mole) of 4'-hydroxy-3'-(methylthio)acetophenone 4'-acetate and 9 g. of calcium carbonate in 300 ml. of chloroform was added dropwise over a period of two hours a solution containing 6 ml. (0.108 mole) of bromine in 30 ml. of chloroform. The reaction mixture was filtered, and the filtrate washed with saturated aqueous sodium bicarbonate, and evaporated to dryness. The residue was dissolved in ether and the ethereal solution diluted with cyclohexane and cooled in ice. The resulting precipitate was collected and dried to give 26.5 g. of 2-bromo-4'-hydroxy-3'-(methylthio)acetophenone 4'-acetate.

D. To a stirred solution containing 13.5 ml. (0.132 mole) of tert-butylamine in 60 ml. of DMF at −65° C. was added dropwise over a period of 45 minutes a solution containing 10.0 g. (0.033 mole) of 2-bromo-4'-hydroxy-3'-(methylthio)acetophenone 4'-acetate in 20 ml. of DMF. After the addition was complete stirring was continued an additional hour at −65° C. The reaction mixture was then treated with 6 ml. of 12 N hydrochloric acid and diluted with methylene chloride. After washing thoroughly with water the methylene chloride solution was dried over anhydrous sodium sulfate, acidified with ethereal hydrogen chloride and concentrated. The resulting precipitate was triturated with ether and collected to give, after drying, 7.5 g. of 2-(tert-butylamino)-4'-hydroxy-3'-(methylthio)acetophenone 4'-acetate, m.p. 205°–207° C.

EXAMPLE 2

A solution containing 4 g. (0.013 mole) of 2-(t-butylamino)-4'-hydroxy-3'-(methylthio)acetophenone 4'-acetate and 1.8 ml. (0.015 mole) of 30% hydrogen peroxide in 60 ml. of methanol was stirred 4 hours at room temperature and then 0.5 hour at reflux. The reaction mixture was then evaporated to dryness and the residue dissolved in methylene chloride. After drying over anhydrous sodium sulfate the methylene solution was acidified with methanesulfonic acid and concentrated. The resulting precipitate was recrystallized twice from 2-propanol-acetone affording 1.1 g. of 2-(t-butylamino)-4'-hydroxy-3'-(methylsulfinyl)acetophenone methanesulfonate, m.p. 220° C. (dec.).

EXAMPLE 3

To a stirred solution containing 7.9 g. (0.24 mole) of 2-(tert-butylamino)-4'-hydroxy-3'-(methylthio)acetophenone 4'-acetate in 150 ml. of methanol at 0° C. was added 950 mg. (0.025 mole) of sodium borohydride. After 45 minutes the reaction mixture was brought to pH 7 with glacial acetic acid and then evaporated to dryness. The residue was diluted with isopropyl acetate and washed with cold 2 N potassium hydroxide. The isopropyl acetate solution was dried over anhydrous sodium sulfate and evaporated to dryness to give α-[(tert-butylamino)methyl]-4-hydroxy-3-(methylthio)benzenemethanol 4-acetate. Alternatively, the isopropyl acetate solution was concentrated and acidified with ethanolic hydrogen chloride. Addition of a small amount of ethanol and cooling in ice effected crystallization. The product was collected and dried to give 4.5 g. of α-[(tert-butylamino)methyl]-4-hydroxy-3-(methylthio)benzenemethanol 4-acetate hydrochloride, m.p. 182°–183° C.

EXAMPLE 4

A solution containing 3.9 g. (0.013 mole) of α-[(t-butylamino)methyl]-4-hydroxy-3-(methylthio)benzenemethanol 4-acetate and 1.7 ml. (0.015 mole) of 30% hydrogen peroxide in 100 ml. of methanol was stirred overnight at room temperature. An additional 0.1 ml. of 30% hydrogen peroxide was added and stirring continued another 1.5 days. The reaction mixture was then concentrated to a small volume, acidified with methanesulfonic acid, diluted with toluene and evaporated to dryness. The residue was slurried with 2-propanol and evaporated to dryness and the process repeated with isopropyl acetate. The resulting product was recrystallized from methanol-2-propanol and dried over phosphorus pentoxide in a vacuum oven at 90° C. to give 3.5 g. of α-[(t-butylamino)methyl]-4-hydroxy-3-(methylsulfinyl)benzenemethanol methanesulfonate, m.p. 204°–205° C. (dec.).

EXAMPLE 5

A. A solution containing 65 g. of p-ethylanisole and 92 g. of methanesulfonic anhydride in 300 ml. of symtetrachloroethane was heated under reflux 17.5 hours. After washing with hot water the reaction mixture was evaporated to dryness in vacuo leaving 20 g. of dark oil which was combined with the product of two previous runs and distilled under reduced pressure. The fraction boiling at 90°–120° C./0.5 mm. was collected and redistilled through a short Vigreux column. The impurities boiling at 45°–65° C./0.5 mm. were discarded and the pot residue was redistilled. The impurities boiling at 175°–187° C./10 mm. were discarded leaving 30 g. of nearly pure 4-ethyl-2-(methylsulfonyl)anisole.

B. A solution containing 55 g. (0.242 mole) of ammonium persulfate, 520 mg. of silver nitrate and 26 g. (0.121 mole) of 4-ethyl-2-(methylsulfonyl)anisole in 300 ml. of water was stirred at 20° C. After one hour the temperature had risen to 48° C. and after 2.5 hours had dropped to 30° C. The product was extracted with chloroform and after drying over anhydrous sodium sulfate the chloroform extracts were evaporated to dryness. The residue was absorbed on a column of silica gel deactivated with 20% by weight of water. Impurities were washed from the column with ether and the product was eluted with hot methylene chloride to give 18 g. of 4'-methoxy-3'-(methylsulfonyl)acetophenone, m.p. 146°–148° C.

C. To a solution containing 14.5 g. (0.063 mole) of 4'-methoxy-3'-(methylsulfonyl)acetophenone in 200 ml. of chloroform was added dropwise a solution containing 10.2 g. of bromine in 40 ml. of chloroform. After a 0.5 hr. induction period the bromine began to be consumed. When the addition was nearly complete the product began to precipitate. The reaction mixture was diluted with methylene chloride and the resulting solution washed successively with saturated aqueous sodium bicarbonate and water and evaporated to dryness. Recrystallization of the residue from methylene chloride-carbon tetrachloride afforded 17.9 g. of 2-bromo-4'-methoxy-3'-(methylsulfonyl)acetophenone, m.p. 168°–170° C.

D. To a stirred solution containing 18 g. (0.25 mole) of t-butylamine in 50 ml. of N,N-dimethylformamide at −65° C. was added dropwise over 45 minutes a solution containing 17.2 g. (0.056 mole) of 2-bromo-4'-methoxy-3'-(methylsulfonyl)acetophenone in 100 ml. of N,N-dimethylformamide. After addition was complete stirring was continued an additional 40 minutes. The solvents were removed by evaporation in vacuo at 40° C. The residue was acidified with ethereal hydrogen chloride and partitioned between water and methylene chloride. The aqueous layer was evaporated to dryness and the residual solid recrystallized from ethanol to give 12 g. of 2-(t-butylamino)-4'-methoxy-3'-(methylsulfonyl)acetophenone hydrochloride, m.p. 213°–214.5° C.

E. A solution containing 12.8 g. (0.038 mole) of 2-(t-butylamino)-4'-methoxy-3'-(methylsulfonyl)acetophenone hydrochloride in 200 ml. of 48% hydrobromic acid was heated under reflux 7 hours. Following the addition of 100 ml. of glacial acetic acid reflux was continued an additional 8 hours. Solvents were then removed by evaporation in vacuo followed by azeotropic distillation with benzene. The residue was recrystallized from 2-propanol-methanol and then methanol. The crystalline hydrobromide was dissolved in trifluoroacetic acid and the solution evaporated to dryness. This process was repeated successively with trifluoroacetic acid and toluene. The resulting residue was dissolved in N,N-dimethylformamide, treated with a slight excess of methanesulfonic acid, and concentrated to a small volume. The resultant precipitate was collected to give 9.5 g. of 2-(t-butylamino)-4'-hydroxy-3'-(methylsulfonyl)acetophenone methanesulfonate, m.p. 247° C. (dec.). The mother liquors afforded a second crop of 1.5 g.

EXAMPLE 6

A solution containing 9.5 g. (0.025 mole) of 2-(t-butylamino)-4'-hydroxy-3'-(methylsulfonyl)acetophenone methanesulfonate in a warm mixture of 200 ml. of N,N-dimethylformamide and 10 ml. of water was hydrogenated under an initial hydrogen pressure of 50 p.s.i. in the presence of approximately 1 g. of 10% palladium-on-carbon hydrogenation catalyst. After 10 minutes one molar equivalent of hydrogen had been absorbed. The catalyst was then removed by filtration, the filtrate concentrated to a small volume, diluted with 2-propanol and toluene and again concentrated to a small volume. The resulting crystalline precipitate was collected and dried over phosphorus pentoxide in a vacuum oven at 100° C. to give 8.8 g. of α-[(t-butylamino)methyl]-4-hydroxy-3-(methylsulfonyl)benzenemethanol methanesulfonate, m.p. 223° C. (dec.).

Additional examples of benzenemethanols and (lower alkylamino)alkyl phenyl ketones having respectively Formulas I and II hereinabove and which are obtained in accordance with the above described procedures are presented in Table A hereinbelow.

Additional examples of haloketones and the corresponding parent phenyl ketones having respectively Formulas III and IV hereinabove and which are useful intermediates in the preparation of the aminoketones of Formula II (Table A) are presented hereinbelow in Tables B and C. The phenyl ketones of Table C are in turn obtained in accordance with the above-described procedures by acylating the generally known o-(lower alkylthio)phenols with an appropriate acyl halide under Friedel-Crafts conditions followed by esterification of the resulting 3-(lower alkylthio)-4-hydroxyphenyl ketones with an appropriate lower alkanoyl or benzoyl halide according to conventional esterification procedures.

TABLE A

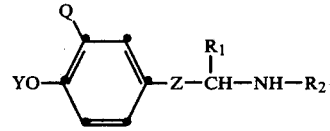

benzenemethanols of Formula I: Z is CHOH
(lower alkylamino)alkyl phenyl ketones of Formula II: Z is C=O

| Q | Y | $R_1$ | $R_2$ |
|---|---|---|---|
| $CH_3SO$ | H | $C_2H_5$ | $CH(CH_3)_2$ |
| $CH_3S$ | H | $C_2H_5$ | $CH(CH_3)_2$ |
| $CH_3S$ | $P-CH_3C_6H_4CO$ | H | $C(CH_3)_3$ |
| $CH_3S$ | $(CH_3)_3CCO$ | H | $C(CH_3)_3$ |
| $CH_3SO$ | $(CH_3)_3CCO$ | H | $C(CH_3)_3$ |
| $C_2H_5SO_2$ | HCO | H | $CH_3$ |
| $CH_3S$ | $C_5H_{11}CO$ | H | $C_2H_5$ |
| $C_2H_5S$ | H | H | $n-C_4H_9$ |
| $C_2H_5SO$ | H | H | $n-C_4H_9$ |
| $n-C_4H_9S$ | H | H | $CH_3$ |
| $CH_3S$ | H | $CH_3$ | $n-C_3H_7$ |

TABLE B

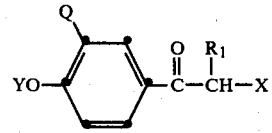

| Q | Y | $R_1$ | X |
|---|---|---|---|
| $CH_3S$ | H | $C_2H_5$ | Br |
| $CH_3S$ | $P-CH_3C_6H_4CO$ | H | Br |
| $CH_3S$ | $(CH_3)_3CCO$ | H | Br |

TABLE B-continued

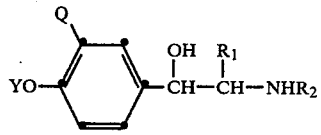

| Q | Y | R₁ | X |
|---|---|---|---|
| $C_2H_5SO_2$ | HCO | H | Cl |
| $CH_3S$ | $C_5H_{11}CO$ | H | Br |
| $C_2H_5S$ | H | H | Br |
| $n$-$C_4H_9S$ | $CH_3CO$ | H | Cl |
| $CH_3S$ | H | $CH_3$ | Br |

TABLE C

| Q | Y | R₁ |
|---|---|---|
| $CH_3S$ | $CH_3CO$ | $C_2H_5$ |
| $CH_3S$ | $P$-$CH_3C_6H_4CO$ | H |
| $CH_3S$ | $(CH_3)_3CCO$ | H |
| $C_2H_5SO_2$ | HCO | H |
| $CH_3S$ | $C_5H_{11}CO$ | H |
| $C_2H_5S$ | $CH_3CO$ | H |
| $n$-$C_4H_9S$ | $CH_3CO$ | H |
| $CH_3S$ | $CH_3CO$ | $CH_3$ |

Representative examples of the compounds of this invention having Formula I have been shown to have useful β-adrenergic blocking activity as determined in the pentobarbitalized dog by the ability of the test compound at a dose of 1.0 mg/kg to inhibit the elevation in heart rate elicited by a 0.5 mg/kg intravenous injection of isoproterenol. The data are presented in Table D hereinbelow:

TABLE D

| β-Adrenergic Blocking Activity | |
|---|---|
| Compound of Example No. | % Inhibition of Heart Rate Elevation |
| 3 | 50 |
| 4 | 100 |
| 6 | 87 |

At the lower doses of 100–200 mcg/kg the compounds of Examples 3 and 4 exhibited β-adrenergic stimulant activity in both respiratory and cardiac smooth muscle as evidenced by their ability to cause a 50% inhibition of the histamine-induced bronchoconstriction in the dog over a period of 2 hours, as well as an increase in heart rate.

The compounds of Examples 3 and 4 also exhibited antihypertensive and vasodilator activity.

Antihypertensive activity was determined on the basis of the observed reduction in systolic blood pressure measured according to the method of H. Kersten et al., J. Lab. and Clin. Med. 32, 1090 (1947) following a single oral medication in the unanesthetized spontaneous hypertensive rat described by Okamato et al., Japan Circulation J. 27, 282 (1963).

Vasodilator activity was judged on the basis of observed reduction in perfusion pressure in the hind limb vasculature of the anesthetized dog determined according to the procedure described by Jandhyala et al. European J. Pharm. 17, 357 (1972), and also on the basis of percent reduction in perfusion pressure as measured in the isolated rabbit ear artery according to the method described by De La Lande et al. Aust. J. Exp. Biol. Med. Sci. 43, 639 (1965).

I claim:

1. A compound having in the free base form the formula:

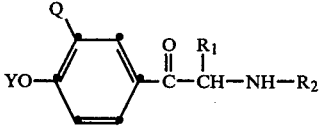

wherein:
- $R_1$ is hydrogen, methyl or ethyl;
- $R_2$ is lower alkyl;
- Q is lower alkylthio or lower alkylsulfinyl; and
- Y is hydrogen, lower alkanoyl, benzoyl or benzoyl substituted with from 1 to 2 methyl groups;

or an acid-addition salt thereof.

2. A compound according to claim 1 wherein $R_1$ is hydrogen.

3. A compound according to claim 2 wherein Q is methylthio or methylsulfinyl.

4. A compound according to claim 3 wherein $R_2$ is tert-butyl.

5. A compound according to claim 4 wherein Y is hydrogen.

6. Alpha-[(tert-butylamino)methyl]-4-hydroxy-3-(methylthio)benzenemethanol 4-acetate or an acid-addition salt thereof according to claim 4.

7. Alpha-[(tert-butylamino)methyl]-4-hydroxy-3-(methylsulfinyl)benzenemethanol or an acid-addition salt thereof according to claim 5.

8. A compound having in the free base form the formula:

wherein:
- $R_1$ is hydrogen, methyl or ethyl;
- $R_2$ is lower alkyl;
- Q is lower alkylthio or lower alkylsulfinyl; and
- Y is hydrogen, lower alkanoyl, benzoyl or benzoyl substituted with from 1 to 2 methyl groups;

or an acid-addition salt thereof.

9. A compound according to claim 8 wherein $R_1$ is hydrogen.

10. A compound according to claim 9 wherein Q is methylthio or methylsulfinyl.

11. A compound according to claim 10 wherein $R_2$ is tert-butyl.

12. A compound according to claim 11 wherein Y is hydrogen.

13. 2-(tert-Butylamino)-4'-hydroxy-3'-(methylthio)acetophenone 4'-acetate or an acid-addition salt thereof according to claim 11.

14. 2-(tert-Butylamino)-4'-hydroxy-3'(methylsulfinyl)acetophenone or an acid-addition salt thereof according to claim 12.

* * * * *

UNITED STATES PATENT AND TRADEMARK OFFICE
CERTIFICATE OF CORRECTION

PATENT NO. : 4,327,224
DATED : April 27, 1982
INVENTOR(S) : Sydney Archer

It is certified that error appears in the above-identified patent and that said Letters Patent is hereby corrected as shown below:

Column 3, line 14

"4-YP" should read -- 4-YO --.

Column 4, line 3

"$R_213NH_2$" should read -- $R_2-NH_2$ --.

Column 5, line 13 the "b" before -- 65°C. -- should be deleted.

Signed and Sealed this

Fifth Day of November 1985

[SEAL]

Attest:

Attesting Officer

DONALD J. QUIGG

Commissioner of Patents and Trademarks